(12) United States Patent
Isogai et al.

(10) Patent No.: US 7,354,152 B2
(45) Date of Patent: Apr. 8, 2008

(54) OPHTHALMIC APPARATUS

(75) Inventors: Naoki Isogai, Nishio (JP); Noriji Kawai, Gamagori (JP); Yutaka Omori, Gamagori (JP)

(73) Assignee: Nidek Co., Ltd. (JP)

( * ) Notice: Subject to any disclaimer, the term of this patent is extended or adjusted under 35 U.S.C. 154(b) by 438 days.

(21) Appl. No.: 10/678,304

(22) Filed: Oct. 6, 2003

(65) Prior Publication Data
US 2004/0066488 A1 Apr. 8, 2004

(30) Foreign Application Priority Data
Oct. 8, 2002 (JP) .............................. 2002-294998

(51) Int. Cl.
*A61B 3/14* (2006.01)
*A61B 3/00* (2006.01)
(52) U.S. Cl. ....................................... 351/206; 351/200
(58) Field of Classification Search ................ 351/204, 351/205–210
See application file for complete search history.

(56) References Cited

U.S. PATENT DOCUMENTS

| 4,854,691 | A |   | 8/1989  | Sekine et al. |
|-----------|---|---|---------|--------------|
| 5,237,350 | A |   | 8/1993  | Sano |
| 5,309,186 | A |   | 5/1994  | Mizuno |
| 5,469,233 | A | * | 11/1995 | Katsuragi ................... 351/205 |
| 5,563,667 | A |   | 10/1996 | Isogai et al. |
| 5,706,072 | A | * | 1/1998  | Kawamura .................. 351/209 |
| 5,708,494 | A |   | 1/1998  | Iijima et al. |
| 5,767,940 | A |   | 6/1998  | Hayashi et al. |
| 6,056,404 | A |   | 5/2000  | Naoki et al. |
| 6,079,828 | A | * | 6/2000  | Fujieda ....................... 351/206 |
| 6,120,149 | A |   | 9/2000  | Hosoi |
| 6,334,682 | B1| * | 1/2002  | Takai .......................... 351/206 |

FOREIGN PATENT DOCUMENTS

| JP | 61-185247 A1 | 8/1986 |
| JP | 06-281726 S  | 10/1994 |

(Continued)

OTHER PUBLICATIONS

EPO Search Report Apr. 21, 2004.

(Continued)

*Primary Examiner*—Scott J. Sugarman
*Assistant Examiner*—DaWayne A Pinkney
(74) *Attorney, Agent, or Firm*—Rader Fishman & Grauer PLLC; Ronald P. Kananen

(57) ABSTRACT

An ophthalmic apparatus capable of checking the presence of abnormality such as soil on optical members and checking before examination whether or not the apparatus is in a state of being affected by disturbance light. The apparatus has a photo-receiving optical system, being arranged inside the apparatus and having optical members, for photo-receiving examination light reflected from the eye which is at an examination position outside the apparatus, a projection optical system, being arranged inside the apparatus and having a light source, for projecting detection light onto the optical member arranged nearest to the outside of the apparatus, a photodetector for photo-receiving reflected detection light when the light source is lit in a state where the eye is not placed at the examination position, and an abnormality detection device for detecting abnormality of the optical members based on an output signal from the photodetector.

18 Claims, 3 Drawing Sheets

| | FOREIGN PATENT DOCUMENTS | | | JP | 2001-211449 S | 8/2001 |

| | | |
|---|---|---|
| JP | 7-39516 A1 | 2/1995 |
| JP | 07-067840 S | 3/1995 |
| JP | 07-124109 S | 5/1995 |
| JP | 8-150116 A1 | 6/1996 |
| JP | 2000-254098 A | 9/2000 |

OTHER PUBLICATIONS

Partial EPO Search Report Jan. 22, 2004.
Office Action mailed on Dec. 7, 2006 (Japan).

* cited by examiner

OPHTHALMIC APPARATUS

BACKGROUND OF THE INVENTION

1. Field of the Invention

The present invention relates to an ophthalmic apparatus which performs examination of an eye to be examined (including measurement of eye characteristics, photographing of an eye portion, and the like).

2. Description of Related Art

In an ophthalmic apparatus such as an eye refractive power measurement apparatus, a corneal shape measurement apparatus, a noncontact tonometer, and a fundus camera, if soil and the like are adhering to optical members such as an examination window and an objective lens, examination results are not obtained (error), or even if obtained, their reliability is lowered. Conventionally, as a remedy for these situations, an instruction manual gives a direction that a protection cap against soil is mounted on the examination window, or a soil check is periodically made. Further, a technique for detecting the soil on the optical members of the apparatus is proposed where a lens cap having a mirror covers the front of the examination window (Japanese Patent Application Unexamined Publication No. Sho61-185247), and alignment light reflected from an eye to be examined is utilized (Japanese Patent Application Unexamined Publication No. Hei7-39516).

Furthermore, also in a case where disturbance light such as sunlight and interior illumination light enters a photo-receiving system inside the apparatus, the examination results are influenced. Therefore, the instruction manual also gives a direction about an installation location of the apparatus.

However, the mounting of the protection cap and the checking of the soil are often forgotten and troublesome. Similarly, the method of detecting the soil by putting the lens cap having the mirror on the front of the examination window is also often forgotten and troublesome. Further, the method of detecting the soil by utilizing the alignment light reflected from the eye cannot be performed in a state where the eye is not placed before the examination.

Furthermore, an operator often does not notice the influence of the disturbance light, and misinterprets abnormality in the examination results and a malfunction as a failure without specifying the disturbance light as a cause for them.

SUMMARY OF THE INVENTION

An object of the invention is to overcome the problems described above and to provide an ophthalmic apparatus capable of checking before examination the presence of abnormality such as soil on optical members and checking before examination whether or not the apparatus is in a state of being affected by disturbance light.

To achieve the objects and in accordance with the purpose of the present invention, an ophthalmic apparatus has a photo-receiving optical system, being arranged on an inside of the apparatus and having optical members, for photo-receiving examination light reflected from the eye which is at an examination position on an outside of the apparatus, a projection optical system, being arranged on the inside of the apparatus and having a light source, for projecting detection light onto the optical member arranged nearest to the outside of the apparatus, a photodetector for photo-receiving reflected detection light when the light source is lit in a state where the eye is not placed at the examination position, and an abnormality detection device for detecting abnormality of the optical members based on an output signal from the photodetector.

In another aspect of the present invention, an ophthalmic apparatus has a photo-receiving optical system, being arranged on an inside of the apparatus, for photo-receiving examination light reflected from the eye which is at an examination position on an outside of the apparatus, a photodetector arranged at a position capable of photo-receiving light entering the inside of the apparatus, and a disturbance light detection device for detecting disturbance light entering the inside of the apparatus based on an output signal from the photodetector in a state where the eye is not placed at the examination position.

Additional objects and advantages of the invention are set forth in the description which follows, are obvious from the description, or may be learned by practicing the invention. The objects and advantages of the invention may be realized and attained by the ophthalmic apparatus in the claims.

BRIEF DESCRIPTION OF THE DRAWINGS

The accompanying drawings, which are incorporated in and constitute apart of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
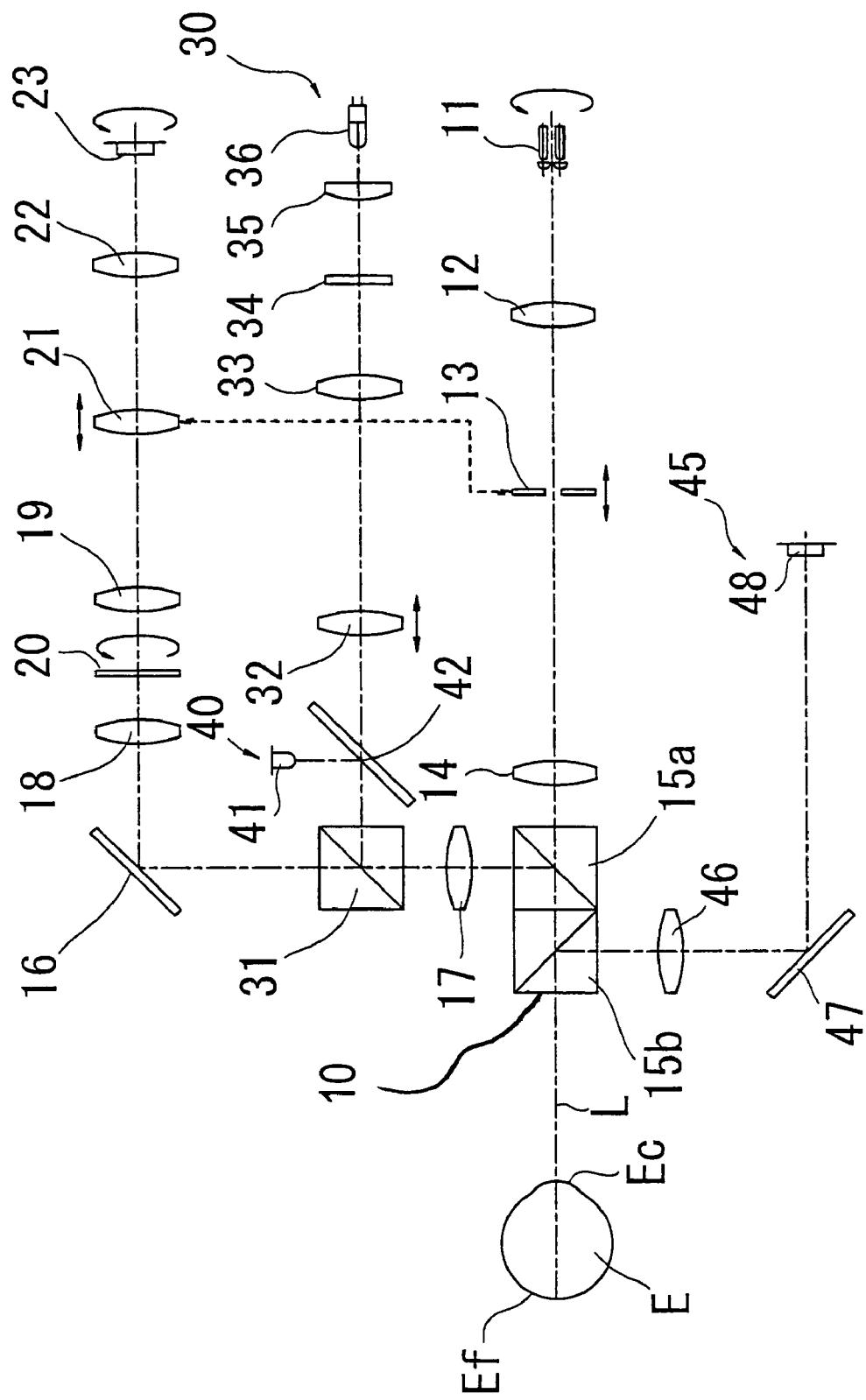
FIG. 1 is a view showing a schematic configuration of an optical system in an eye refractive power measurement apparatus.

A detailed description of one preferred embodiment of an ophthalmic apparatus embodied by the present invention is provided below with reference to the accompanying drawings. FIG. 1 is a view showing a schematic configuration of an optical system in an eye refractive power measurement apparatus.

Two light sources 11 for measurement (examination) emit near infrared measurement light (examination light), and are arranged rotatable about an optical axis L. Reference numeral 12 indicates a condenser lens. A target plate 13 for measurement (examination) has a target for measurement (examination) (a spot aperture) and is movable on the optical axis L so as to be arranged at a position conjugate with a fundus Ef of an eye E to be examined. Reference numeral 14 indicates a projecting lens, and 15a and 15b indicate half mirrors. Reference numeral 17 indicates an objective lens, 31 indicates a half mirror, 16 indicates a mirror, and 18 and 19 indicate relay lenses. A corneal reflection elimination mask 20 in a strip shape is arranged at a position conjugate with a cornea Ec of the eye E. A mobile lens 21 is movable on the optical axis L in conjunction with the target plate 13. Reference numeral 22 indicates an image forming lens. A photodetector 23 for measurement (examination) is arranged to be rotatable about the optical axis L in synchronization with the light source 11 and the mask 20. In this apparatus, a surface of the half mirror 15b on the eye E side is a window 10 for measurement (examination). For information, the window for measurement described here is a transparent member which separates the inside and the outside of the apparatus, and for example, a glass plate for protection or the like may be provided as the measurement window on the eye E side of the half mirror 15b.

Reference numeral 30 indicates a fixation target presenting optical system. A first relay lens 32 is movable on the optical axis L. Reference numeral 33 indicates a second relay lens. A fixation target 34 is arranged at a focal point of the lens 33. Reference numeral 35 indicates a condenser lens. A target illumination light source 36 emits visible light. The lens 32 moves on the optical axis L to optically change a presenting position (a distance) of the fixation target 34, and performs fogging for suppressing accommodation of the eye E at the time of eye refractive power measurement.

An alignment index projection optical system 40 projects an index for alignment from a visual axis direction of the eye E. A point light source 41 emits infrared light being the alignment index. The light emitted from the light source 41 is reflected by a dichroic mirror 42 having a property of transmitting visible light and reflecting infrared light. Then, the light passes through the half mirror 31 and is formed into a parallel light bundle by the lens 17. And then, the light passes through the half mirrors 15a and 15b to project the alignment index from the front of the eye E along the optical axis L.

Reference numeral 45 indicates an observation optical system. An image of an anterior segment (reflection light from the anterior segment) of the eye E illuminated by an infrared light source for anterior segment illumination not illustrated, and an image of the alignment index (a corneal reflection image of the light source 41) pass through the half mirror 15b, an objective lens 46 and a mirror 47 to be picked up by (photo-received on) a CCD camera 48 as an image pickup element.

Figure 2:
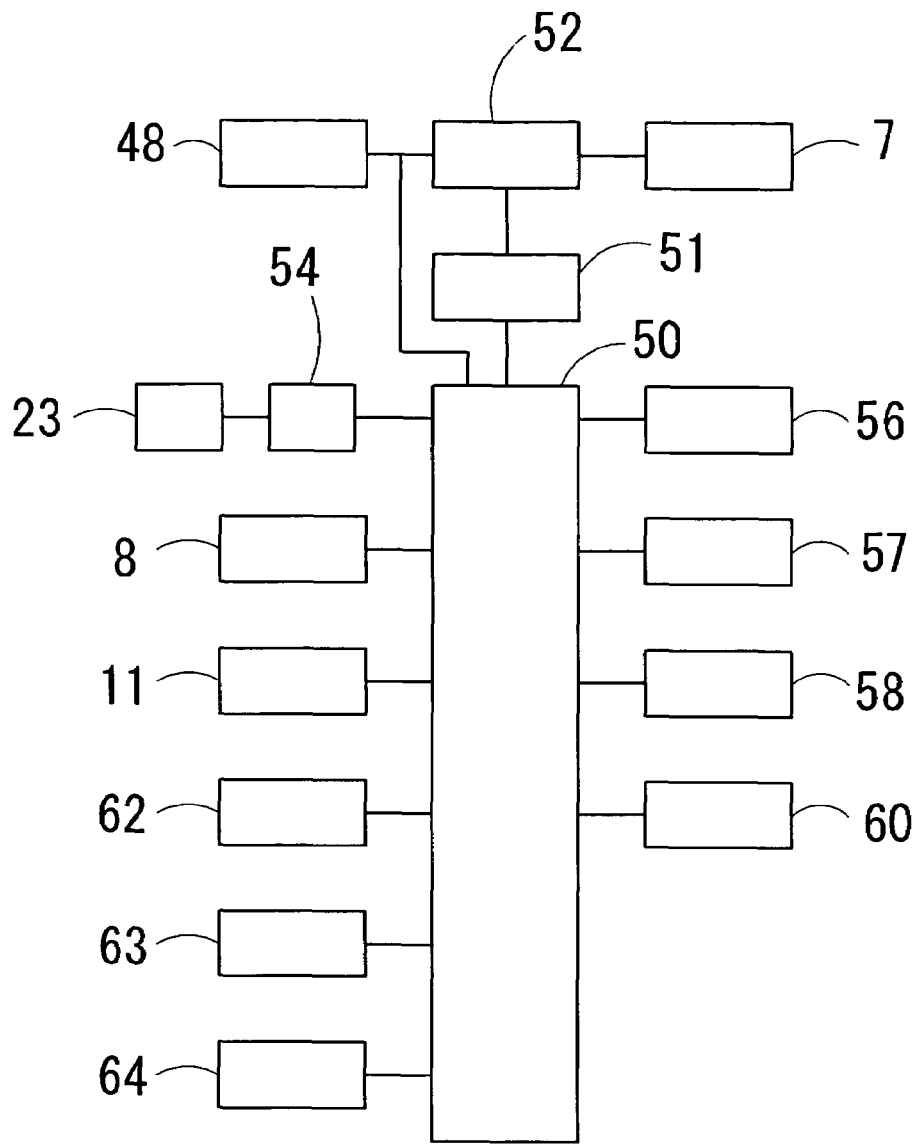
FIG. 2 is a view showing a schematic configuration of a control system in the present apparatus.

FIG. 2 is a view showing a schematic configuration of a control system in the present apparatus. A synthesizing circuit 52 combines an image signal from the camera 48 with a character signal and a graphic signal which are generated in a display circuit 51 to be displayed on a TV monitor (display) 7. Reference numeral 50 indicates a control unit. An output signal from the photodetector 23 is processed through a signal processing circuit 54 and inputted to the control unit 50. The control unit 50 is connected with a switch unit 8, the light sources 11, a motor 56 for rotating the light sources 11, the mask 20, and the photodetector 23, a motor 57 for moving the target plate 13 and the lens 21, a motor 58 for moving the lens 32, a potentiometer 60 for detecting a travel position of the target plate 13 (or the lens 21), a memory 62, a power switch 63 and the like.

The eye refractive power measurement performed by the apparatus having a constitution as above will be described. The measurement light emitted from the light source 11 passes through the lens 12, the target plate 13, the lens 14, and the half mirrors 15a and 15b (the window 10), and is collected in the vicinity of the cornea Ec, and then reaches the fundus Ef. In a case where the eye E is emmetropia, light of a measurement target image reflected by the fundus Ef passes through the half mirrors 15b and 15a, the lens 17, the half mirror 31, the mirror 16, the lenses 18 and 19, and the lens 22 to form an image on the photodetector 23. In a case where the eye E is ametropia, based on the output signal from the photodetector 23, the motor 57 is driven to move the target plate 13 and the lens 21 to be positioned at the positions conjugate with the fundus Ef.

The motor 58 is driven to move the lens 32 so that the fixation target 34 is placed at a position conjugate with the fundus Ef, and then the lens 32 is further moved so that the fogging is performed by the amount of appropriate diopter. Then, in a state where the eye E is fogged, the light sources 11, the mask 20, and the photodetector 23 are rotated 180° about the optical axis L. During the rotation, the target plate 13 and the lens 21 are moved based on the output signal from the photodetector 23, and the potentiometer 60 detects a travel amount to obtain a value on refractive power in each meridian direction. The control unit 50 provides the refractive power with a predetermined processing to obtain objective values of S (spherical refractive power), C (astigmatic power) and A (an astigmatic axial angle).

Next, soil detection and disturbance light detection in the optical system will be described. When the power switch 63 to the apparatus is turned on in a state where a reflection object such as the eye E and a model eye is not placed in front of the window 10, initialization is implemented, and then a soil detection mode is activated. When the soil detection mode is activated, a message "Under a soil check" is displayed on the monitor 7. The control unit 50 drives the motor 57 to move the lens 21 and the target plate 13 at predetermined positions such as positions for emmetropia (positions for 0D) to light the light sources 11. At this time, the light source 11 blinks at a predetermined frequency. The measurement light emitted from the light source 11 passes through the lens 12, the target plate 13, and the lens 14 to head for the half mirrors 15a and 15b. The reflection light from the window 10 passes through from the half mirror 15b to the lens 22 as in the case of the reflection light from the fundus Ef at the time of the eye refractive power measurement, and is photo-received on the photodetector 23. The control unit 50 compares an output signal level of the photodetector 23, which is inputted through the signal processing circuit 54, with a predetermined reference level (an output signal level in a state where the eye is not placed), and checks the presence of an abnormal output signal beyond the reference level. In a case where the window 10 is soiled, light intensity of the reflection light at the soiled portion is increased, and this light enters the photodetector 23 to be detected as the abnormal output signal.

Besides, also in the case of the soil detection, the control unit 50 rotates the light sources 11, the mask 20 and the photodetector 23 180° about the optical axis L as in the case of the measurement. Thereby, the detection light may be projected over a wide range of the window 10 to check the soil and the like. In addition, if the mask 20 is also provided with a photodetector, the mask 20 may also check the presence of the abnormal output signal to finely detect the soil and the like.

When the abnormal output signal is detected, the control unit 50 displays a warning message such as "Please clean the measurement window." on the monitor 7. At the same time, a sound generator not illustrated informs an operator of that message by way of an alarm, a voice guide or the like. Then, the operator cleans the window 10, and performs the soil detection operation again using a switch in the switch unit 8 in a state where the reflection object is not placed in front of the window 10. If the abnormal output signal is not detected, a message "OK" is displayed to finish the soil detection mode.

Incidentally, the reference level described above may be determined by experiment and the like, or an operation similar to that in the soil detection mode may be performed as adjustment at the time of manufacture of the apparatus, and an output signal level at that time may be stored. Also for the positions to which the target plate 13 and the lens 21 are moved, positions in which the light intensity of the reflection light due to the soil on the window 10 is easily detected may be previously obtained by experiment. By moving the lens 21, a portion conjugate with the photodetector 23 may be changed, and a portion to detect the soil or the abnormal reflection may be changed. Besides, the photodetector 23 may be moved on the optical axis L instead of moving the lens 21.

Further, the target plate 13 and the lens 21 are moved over a whole motion (travel) range, and the output signal from the photodetector 23 is checked as well, so that the presence of the abnormal reflection due to the soil and the like on other optical members in a photo-receiving optical system including the window 10 may be detected. In a case where a portion to be checked for the soil and the like is previously determined, it is efficient that the lens 21 is moved toward a corresponding position for checking. The checking may be performed at a time in the soil detection mode, or may be separately performed on another setting. In addition, according to the abnormal output signal level of the photodetector 23, a degree of abnormality of the soil and the like is expressed in a scale of 1 to 5 and the like, so that the operator may easily determine timing of a routine check.

When the soil detection mode is finished, a disturbance light detection mode sequentially proceeds to check whether or not the disturbance light such as sunlight and interior illumination light enters a photo-receiving system. The output signal level of the photodetector 23 is checked while rotating the light sources 11, the mask 20 and the photodetector 23 as stated above without lighting the light sources 11. Preferably, the checking is performed while the lens 21 is moved over the whole motion range. In a case where, even though the light sources 11 are not lit, an abnormally strong output signal is obtained from the photodetector 23 or the photodetector arranged in the mask 20 (in a case where the output signal is compared with a reference level for disturbance light detection which is determined separately from the reference level for the soil detection, and an output signal level beyond the reference level is obtained), it is judged that the disturbance light enters, and a message such as "Disturbance light is entering. Please change direction of the measurement Window." is displayed on the monitor 7. Further, an alarm indicating the message is given by the sound generator to inform the operator of it.

The operator removes a factor causing the disturbance light, and then performs again the disturbance light detection operation using the switch in the switch unit 8. If there is no abnormality, a message "OK" is displayed, and the disturbance light detection is finished and shifted into a standby mode in which measurement may be started. In a case where the abnormal output signal level of the photodetector 23 (and the other photodetector) is detected in a state where the disturbance light does not actually enter, failure in an electric circuit and the like is conceivable. Therefore, this fact may be annunciated.

Figure 3:
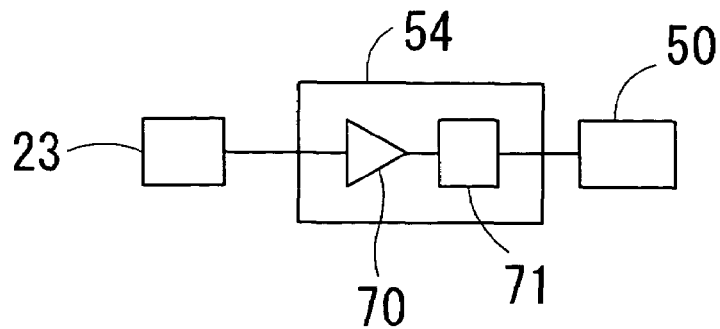
FIG. 3 is a view showing an example of a signal processing circuit for discriminating disturbance light such as sunlight and fluorescent light for signal detection in soil detection.

As for the signal detection in the soil detection mentioned above, the reflection light from the window 10 may be detected while discriminating the sunlight or the fluorescent light to some degree by the signal processing circuit 54. FIG. 3 is a view showing an example of the signal processing circuit 54 with an amplifier 70 and a filter circuit 71. The light source 11 blinks at a high frequency of 1 KHz. The output signal from the photodetector 23 is amplified by the amplifier 70 and sent to the filter circuit 71. Then, the filter circuit 71 performs a role of not transmitting a signal with a frequency component lower than 1 KHz or with a DC component and transmitting only a signal with a high frequency component from the light source 11. The sunlight is mainly of the DC component, and the interior illumination light emitted from the fluorescent lamp is a signal with a low frequency component of 60 Hz and the like, so that these light may be cut off. It is more preferable that the filter circuit 71 is a band pass filter, and the light with a frequency component higher than 1 KHz, e.g. the light with a high frequency component of 10 KHz and the like emitted from a fluorescent lamp of an inverter type is cut off. The control unit 50 compares an output signal level through the filter circuit 71 with the reference level, and detects any output signal above the reference level as abnormality.

Incidentally, for the light source and the photodetector used for the soil detection and the disturbance light detection, dedicated ones may be employed. However, if the light source for measurement and the photodetector for measurement are shared as stated above, the constitution does not become complicated and becomes economically advantageous.

In addition, except for the light source for measurement and the photodetector for measurement, other light sources and photodetectors (sensors) provided inside the apparatus may be shared. For example, the present apparatus may employ the light source 41 for alignment and the camera 48 for observation (for photo-receiving the alignment light). The alignment light emitted from the light source 41 is also reflected by the window 10 if the window 10 is soiled. The reflection light passes through the half mirror 15b, the lens 46 and the mirror 47 to be photo-received on the camera 48. In the case of the soil detection mode, the control unit 50 controls the lighting of the light source 41, and checks an output signal level of light intensity photo-received on the camera 48 when the light source 41 is lit and when it is not lit.

Figure 4:
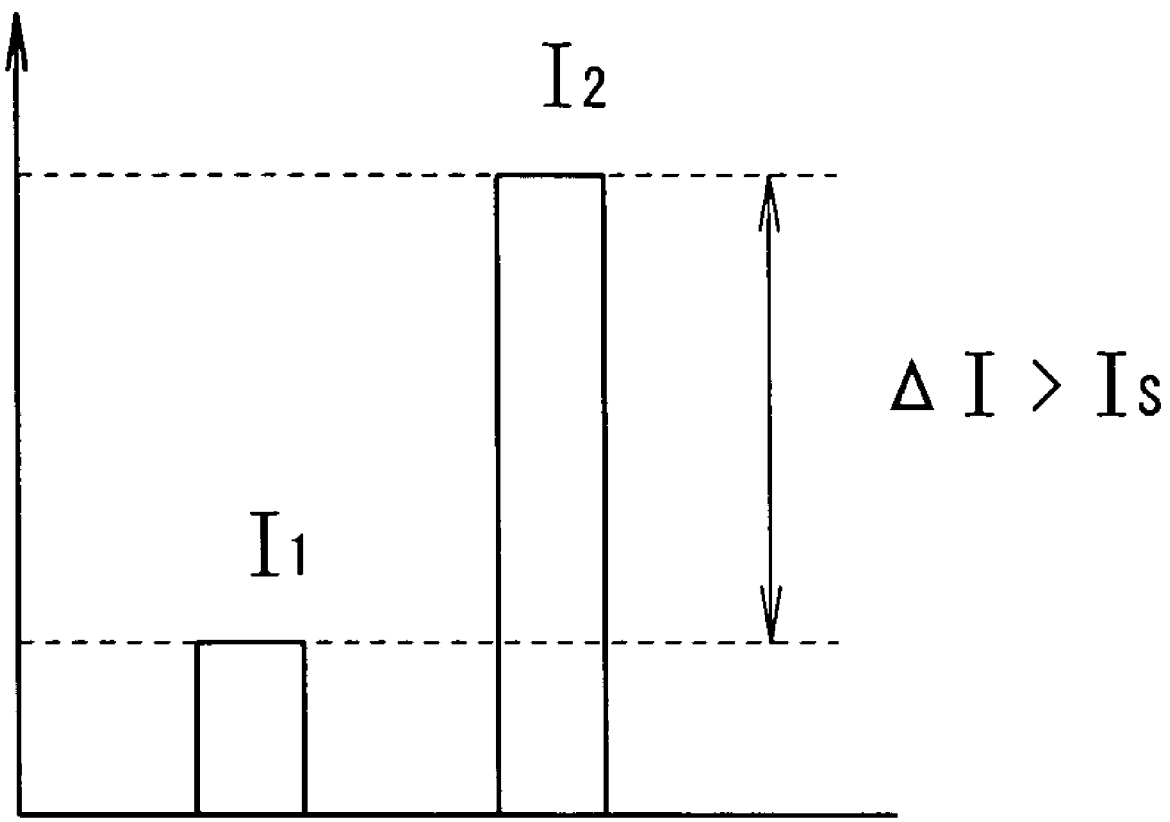
FIG. 4 is a view showing an example of an output signal which presents intensity of light photo-received on a CCD camera when a light source is lit and when it is not lit.

FIG. 4 is a view showing an example of the output signal presenting the intensity of light photo-received on the camera 48 when the light source 41 is lit and when it is not lit. Reference numeral I1 is an output signal level when the light source 41 is not lit, and in this case, there is no reflection light from the window 10, and I1 becomes the signal level of the disturbance light entering from the window 10. Reference numeral I2 indicates an output signal level when the light source 41 is lit, wherein the reflection light from the window 10 and the disturbance light entering the window 10 are summed. Accordingly, a difference ΔI between I1 and I2 becomes the signal level of the reflection light from the window 10, and if the window 10 is soiled, the signal level of ΔI is increased. The control unit 50 compares ΔI with a predetermined reference level Is, and detects abnormality if ΔI is beyond Is. In the case of a two-dimensional photodetector (sensor), averaged light intensity is taken into consideration for judgment, or judgment may be made for each two-dimensional place. Of course, this detection method may be applied also to the case of using the light sources 11 and the photodetector 23, and only the abnormality in the optical members such as the soil may be easily detected while discriminating the disturbance light. The reference signal level Is may be determined by experiment, or an operation similar to the soil detection mode may be performed as adjustment at the time of the manufacture of the apparatus, and an output signal level at this time may be stored. In the disturbance light detection mode, the output signal level of the camera 48 when the light source 41 is not lit may be observed. Besides, in a case where an image pickup element such as the camera 48 is used as the photodetector, abnormal reflection light may be detected through image analysis.

The operation in the soil detection mode and the disturbance light detection mode mentioned above may be performed every time a signal is generated by a print switch arranged in the switch unit 8, or every time new measurement takes place for a new examinee, and the like. If the detection takes much time, the number of measurement for the examinee is counted, and the operation may be performed at every given number (for example, every ten measurement). In addition, a clock function 64 provided to the apparatus may be used to perform the operation at a predetermined time or at predetermined intervals (at a time nearest to the predetermined time, when the apparatus is firstly turned on at one day, or at other times). Furthermore, apart from this, it is convenient that a mode switch for implementing these detection modes is provided because the operator may optionally implement the operation at a stage when the soil and the like become annoying.

In addition, in the soil detection mode and the disturbance light detection mode in which the operation is implemented by the power switch 63 to the apparatus or automatically implemented at the time under the predetermined condition, only the measurement window or a portion into which the disturbance light is easy to enter are detected, so that the operation is completed in short time. In addition, it is preferable that a mode for making a more fine check is made may be selected by the switch operation.

A request of a user may be satisfied if a variety of settings including the detection method in the soil detection mode and the disturbance detection mode (to implement or not, to what degree to implement, timing of implementation, and the like), and its informing method (informing by the display and the sound) may be set by the switch operation.

An example in which the present invention is applied to the eye refractive power measurement apparatus is given above. However, the present invention may be applied to a variety of ophthalmic apparatuses such as a corneal shape measurement apparatus, a noncontact tonometer, and a fundus camera. In addition, the present invention may be applied to a lens meter.

As described above, according to the present invention, the condition of the apparatus may be checked as to whether or not the abnormality such as the soil presents on the optical members, or whether or not the apparatus is in the state of being affected by the disturbance light.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus for examining an eye to be examined, the apparatus comprising:
   a photo-receiving optical system, being arranged on an inside of the apparatus and having optical members, for photo-receiving examination light reflected from the eye which is at an examination position on an outside of the apparatus;
   a projection optical system, being arranged on the inside of the apparatus and having a light source, for projecting detection light toward at least one of the optical members that is arranged nearest to the outside of the apparatus;
   a photodetector for photo-receiving reflected detection light when the light source is lit in a state where the eye is not placed at the examination position; and
   abnormality detection means for detecting abnormality of the at least one of the optical members based on an output signal from the photodetector, wherein
   the light source blinks at a predetermined high frequency, and
   the abnormality detection means includes a filter circuit which transmits only a signal with a high frequency component form the light source.

2. The ophthalmic apparatus according to claim 1, wherein the abnormality detection means detects the abnormality based on a result of comparison between an output signal level of the photodetector when the light source is lit and a reference level.

3. The ophthalmic apparatus according to claim 1, wherein the abnormality detection means obtains a difference between an output signal level of the photodetector when the light source is lit and an output signal level of the photodetector when the light source is not lit, and detects the abnormality based on a result of comparison between the obtained difference and a reference level.

4. The ophthalmic apparatus according to claim 1, wherein
   the photodetector includes an image pickup element, and
   the abnormality detection means detects the abnormality by analyzing an image picked up by the image pickup element.

5. The ophthalmic apparatus according to claim 1, wherein
   the projection optical system includes any one of an optical system for projecting the examination light onto the eye and an optical system for projecting alignment light onto the eye, and
   the photodetector includes any one of a photodetector for photo-receiving the examination light in the photo-receiving optical system and a photodetector for photo-receiving the alignment light.

6. The ophthalmic apparatus according to claim 1, further comprising a rotation unit which rotates the light source and the photodetector in synchronization about an optical axis.

7. The ophthalmic apparatus according to claim 1, further comprising a mobile lens for changing a position conjugate with the photodetector.

8. The ophthalmic apparatus according to claim 1, wherein one of the optical members, which is arranged nearest to the outside of the apparatus, includes a transparent member for separating the inside and the outside of the apparatus.

9. The ophthalmic apparatus according to claim 1, further comprising disturbance light detection means for detecting disturbance light entering from the outside based on an output signal from the photodetector when the light source is not lit.

10. An ophthalmic apparatus for examining an eye to be examined, the apparatus comprising:
    a transparent window for separating an inside and an outside of the apparatus;

an examination light projecting optical system, having a first light source and being arranged on the inside, for projecting examination light onto the eye which is at an examination position in front of the window on the outside through the window;

an examination light receiving optical system, having a photodetector and being arranged on the inside, for photo-receiving the examination light reflected from the eye which is at the examination position through the window;

an alignment index light projection optical system, having a second light source and being arranged on the inside, for projecting alignment index light onto the eye which is at the examination position through the window; and an alignment index light receiving optical system, having an image pickup element and being arranged on the inside, for photo-receiving the alignment index light reflected from the eye which is at the examination position through the window;

abnormal reflection detecting means which is activated in a soil detection mode, not a measurement mode, for comparing an output signal level of the photodetector or the image pickup element when the first light source or the second light source is lit in a state where the eye or a reflection object is not placed in front of the window on the outside, with a reference level, and detecting abnormal reflection of the examination light or the alignment index light by soil on the window by checking presence of the output signal level above the reference level; and informing means for informing an operator of a detection result by the abnormal reflection detecting means.

11. The ophthalmic apparatus according to claim 10, wherein the abnormal reflection detecting means obtains a difference between the output signal level of the photodetector or the image pickup element when the first light source or the second light source is lit in the state where the eye or the reflection object is not placed in front of the window on the outside and an output signal level of the photodetector or the image pickup element when the first light source or the second light source is not lit in the state where the eye or the reflection object is not placed in front of the window on the outside, and compares the obtained difference with the reflection level.

12. The ophthalmic apparatus according to claim 10, wherein the photodetector includes an image pickup element.

13. The ophthalmic apparatus according to claim 10, further comprising a rotation unit which rotates the first light source or the second light source and the photodetector or the image pickup element in synchronization about an optical axis.

14. The ophthalmic apparatus according to claim 10, further comprising a mobile lens for changing a position conjugate with the photodetector or the image pickup element.

15. The ophthalmic apparatus according to claim 10, wherein the abnormal reflection detecting means is activated by being placed in the soil detection mode by turning on the apparatus.

16. An ophthalmic apparatus for examining an eye to be examined, the apparatus comprising:

a transparent window for separating an inside and an outside of the apparatus;

an examination optical system arranged on the inside, for projecting examination light onto the eye which is at an examination position in front of the window on the outside through the window and photo-receiving the examination light reflected from the eye which is at the examination position through the window with a photodetector;

an alignment optical system arranged on the inside, for projecting alignment index light onto the eye which is at the examination position through the window and photo-receiving the alignment index light reflected form the eye which is at the examination position through the window with an image pickup element;

a detection light projection optical system for projecting detection light through the window;

abnormal reflection detecting means which is activated in a soil detection mode, not a measurement mode, for comparing an output signal level of the photodetector or the image pickup element when the detection light is projected in a state where the eye or a reflection object is not placed in front of the window on the outside, with a reference level, and detecting abnormal reflection of the detection light by soil on the window by checking presence of the output signal level above the reference level; and informing means for informing an operator of a detection result by the abnormal reflection detecting means.

17. The ophthalmic apparatus according to claim 16, wherein the detection light projection optical system is included in the examination optical system or the alignment optical system, and the detection light is the examination light or the alignment index light.

18. The ophthalmic apparatus according to claim 16, wherein the abnormal reflection detecting means is activated by being placed in the soil detection mode by turning on the apparatus.

* * * * *